(12) United States Patent
Zhang et al.

(10) Patent No.: US 9,268,903 B2
(45) Date of Patent: Feb. 23, 2016

(54) SYSTEMS AND METHODS FOR SEQUENCE DATA ALIGNMENT QUALITY ASSESSMENT

(75) Inventors: Zheng Zhang, Pasadena, CA (US); Sowmi Utiramerur, Cupertino, CA (US); Fiona Hyland, San Mateo, CA (US)

(73) Assignee: Life Technologies Corporation, Carlsbad, CA (US)

( * ) Notice: Subject to any disclaimer, the term of this patent is extended or adjusted under 35 U.S.C. 154(b) by 1043 days.

(21) Appl. No.: 13/177,267

(22) Filed: Jul. 6, 2011

(65) Prior Publication Data

US 2012/0011086 A1  Jan. 12, 2012

Related U.S. Application Data

(60) Provisional application No. 61/361,879, filed on Jul. 6, 2010.

(51) Int. Cl.
 *G06F 19/22* (2011.01)
 *G06F 15/00* (2006.01)
 *G06F 19/24* (2011.01)

(52) U.S. Cl.
 CPC ............... *G06F 19/22* (2013.01); *G06F 19/24* (2013.01)

(58) Field of Classification Search
 CPC ............... C12Q 1/6806; C12Q 1/6869; C12Q 2535/122; G06F 19/18; G06F 19/22; G06F 19/16; G06F 19/366
 See application file for complete search history.

(56) References Cited

U.S. PATENT DOCUMENTS

| | | |
|---|---|---|
| 5,430,886 A | 7/1995 | Furtek |
| 5,504,931 A | 4/1996 | Furtek |
| 5,577,249 A | 11/1996 | Califano |
| 5,598,350 A | 1/1997 | Kawanishi et al. |
| 5,601,982 A | 2/1997 | Sargent et al. |
| 5,604,100 A | 2/1997 | Perlin |
| 5,671,090 A | 9/1997 | Pernick et al. |
| 5,706,498 A | 1/1998 | Fuimiya et al. |
| 5,856,928 A | 1/1999 | Yan |
| 5,873,052 A | 2/1999 | Sharaf |
| 5,891,632 A | 4/1999 | Imai |
| 5,964,860 A | 10/1999 | Peterson et al. |
| 5,966,711 A | 10/1999 | Adams |
| 6,001,562 A | 12/1999 | Milosavljevic |
| 6,054,276 A | 4/2000 | Macevicz et al. |
| 6,068,977 A | 5/2000 | Perlin |
| 6,117,634 A | 9/2000 | Langmore et al. |
| 6,119,120 A | 9/2000 | Miller |
| 6,143,498 A | 11/2000 | Olsen et al. |
| 6,189,013 B1 | 2/2001 | Maslyn et al. |
| 6,223,128 B1 | 4/2001 | Allex et al. |
| 6,223,175 B1 | 4/2001 | George et al. |
| 6,223,186 B1 | 4/2001 | Rigault et al. |
| 6,287,773 B1 | 9/2001 | Newell |
| 6,363,399 B1 | 3/2002 | Maslyn et al. |
| 6,383,743 B1 | 5/2002 | Kinzler et al. |
| 6,389,428 B1 | 5/2002 | Rigault et al. |
| 6,404,907 B1 | 6/2002 | Gilchrist et al. |
| 6,421,613 B1 | 7/2002 | Nadimpalli et al. |
| 6,470,277 B1 | 10/2002 | Chin et al. |
| 6,484,105 B2 | 11/2002 | Zhang |
| 6,505,126 B1 | 1/2003 | Hare et al. |
| 6,518,023 B1 | 2/2003 | Brenner |
| 6,528,260 B1 | 3/2003 | Blumenfeld et al. |
| 6,571,230 B1 | 5/2003 | Parida |
| 6,607,888 B2 | 8/2003 | Schwartz et al. |
| 6,635,423 B2 | 10/2003 | Dooley et al. |
| 6,691,109 B2 | 2/2004 | Bjornson et al. |
| 6,708,119 B2 | 3/2004 | Imai et al. |
| 6,713,257 B2 | 3/2004 | Shoemaker et al. |
| 6,714,874 B1 | 3/2004 | Myers et al. |
| 6,721,663 B1 | 4/2004 | Roberts et al. |
| 6,745,130 B2 | 6/2004 | Kawanishi et al. |
| 6,747,643 B2 | 6/2004 | Happel |
| 6,760,668 B1 | 7/2004 | Izmailov et al. |
| 6,775,622 B1 | 8/2004 | Holloway |
| 6,785,614 B1 | 8/2004 | Collins et al. |
| 6,790,658 B2 | 9/2004 | Pecker et al. |
| 6,842,703 B2 | 1/2005 | Newell |
| 6,879,916 B2 | 4/2005 | Nadimpalli |

(Continued)

FOREIGN PATENT DOCUMENTS

WO  WO-2006/084132  8/2006

OTHER PUBLICATIONS

Medvedev et al. Computational methods for discovering structural variation with next-generation sequencing Nature Methods vol. 6, pp. S13-S20 (2009).*
Li et al. Mapping short DNA sequencing reads and calling variants using mapping quality scores Genome Research vol. 18, pp. 1-8 (2008).*
Shendure et al. Next-generation DNA sequencing Nature Biotechnology vol. 26, pp. 1135-1145 (2008).*
Butler et al. ALLPATHS: De novo assembly of whole-genome shotgun microreads Genome Research vol. 18,pp. 810-820 (2008).*
Kent, W., "Assembly of the Working Draft of the Human Genome with GigAssembler", Genome Research,vol. 11, pp. 1541-1548 (2001).
Mullikin, J., "The Phusion Assembler", Genome Research vol. 13, pp. 81-90 (2003).
Roach et al., "Pairwise End Sequencing: A Unified Approach to Genomic Mapping and Sequencing," *Genomics*, 26:345-353 (1995).
Siegel et al., "Modeling the Feasibility of Whole Genome Shotgun Sequencing Using a Pairwise End Strategy," *Genomics*, 68:237-246 (2000).

*Primary Examiner* — John S Brusca (57) ABSTRACT

A computer-implemented method for classifying alignments of paired nucleic acid sequence reads is disclosed. A plurality of paired nucleic acid sequence reads is received, wherein each read is comprised of a first tag and a second tag separated by an insert region. Potential alignments for the first and second tags of each read to a reference sequence is determined, wherein the potential alignments satisfies a minimum threshold mismatch constraint. Potential paired alignments of the first and second tags of each read are identified, wherein a distance between the first and second tags of each potential paired alignment is within an estimated insert size range. An alignment score is calculated for each potential paired alignment based on a distance between the first and second tags and a total number of mismatches for each tag.

13 Claims, 4 Drawing Sheets

(56) References Cited

U.S. PATENT DOCUMENTS

| | | |
|---|---|---|
| 6,898,530 B1 | 5/2005 | Saffer et al. |
| 6,905,837 B2 | 6/2005 | Roberts et al. |
| 6,960,471 B2 | 11/2005 | Pecker et al. |
| 6,961,664 B2 | 11/2005 | Selifonov et al. |
| 6,963,865 B2 | 11/2005 | Bera |
| 6,983,274 B2 | 1/2006 | Patzer |
| 6,988,039 B2 | 1/2006 | Poleksic |
| 6,990,238 B1 | 1/2006 | Saffer et al. |
| 6,994,965 B2 | 2/2006 | Tamura et al. |
| 6,996,474 B1 | 2/2006 | Colinge et al. |
| 6,996,477 B2 | 2/2006 | Meyerson et al. |
| 7,006,924 B2 | 2/2006 | Watanabe et al. |
| 7,007,001 B2 | 2/2006 | Oliver et al. |
| 7,039,238 B2 | 5/2006 | Sonmez et al. |
| 7,041,455 B2 | 5/2006 | Magness et al. |
| 7,043,371 B2 | 5/2006 | Wheeler et al. |
| 7,054,755 B2 | 5/2006 | O'Reilly et al. |
| 7,058,634 B2 | 6/2006 | Potts et al. |
| 7,061,491 B2 | 6/2006 | Happel |
| 7,065,451 B2 | 6/2006 | Garner et al. |
| 7,078,504 B2 | 7/2006 | Short et al. |
| 7,085,651 B2 | 8/2006 | Yasuda et al. |
| 7,085,652 B2 | 8/2006 | Scaf et al. |
| 7,099,777 B1 | 8/2006 | Ghandour et al. |
| 7,125,662 B2 | 10/2006 | Hall et al. |
| 7,133,781 B2 | 11/2006 | Toll et al. |
| 7,141,418 B2 | 11/2006 | Kunsch et al. |
| 7,181,373 B2 | 2/2007 | Le Cocq et al. |
| 7,205,111 B2 | 4/2007 | Christensen et al. |
| 7,217,509 B2 | 5/2007 | Wolffe et al. |
| 7,231,390 B2 | 6/2007 | Blair et al. |
| 7,254,489 B2 | 8/2007 | Mossel |
| 7,263,444 B2 | 8/2007 | Clark |
| 7,313,555 B2 | 12/2007 | Klier |
| 7,325,013 B2 | 1/2008 | Caruso |
| 7,328,111 B2 | 2/2008 | Porikli |
| 7,333,980 B2 | 2/2008 | Bjornson et al. |
| 7,365,164 B2 | 4/2008 | Naka et al. |
| 7,386,523 B2 | 6/2008 | Diao |
| 7,396,646 B2 | 7/2008 | Quinlan et al. |
| 7,400,980 B2 | 7/2008 | Liu et al. |
| 7,424,369 B2 | 9/2008 | Braun et al. |
| 7,424,371 B2 | 9/2008 | Kamentsky |
| 7,424,464 B2 | 9/2008 | Oliver et al. |
| 7,444,243 B2 | 10/2008 | McIninch |
| 7,451,123 B2 | 11/2008 | Platt et al. |
| 7,474,759 B2 | 1/2009 | Sternberg et al. |
| 7,475,087 B1 | 1/2009 | Lazo et al. |
| 7,512,498 B2 | 3/2009 | Pentkovski |
| 7,539,579 B2 | 5/2009 | Beattie et al. |
| 7,584,058 B2 | 9/2009 | Zabeau et al. |
| 7,590,291 B2 | 9/2009 | Bradski et al. |
| 7,593,818 B2 | 9/2009 | Zabeau et al. |
| 7,599,802 B2 | 10/2009 | Harwood et al. |
| 7,604,998 B2 | 10/2009 | Elliott |
| 7,606,403 B2 | 10/2009 | Haussecker et al. |
| 7,614,036 B2 | 11/2009 | Bjornson et al. |
| 7,627,537 B2 | 12/2009 | Lai |
| 7,657,382 B2 | 2/2010 | Kwon et al. |
| 7,680,601 B1 | 3/2010 | Khosla et al. |
| 7,680,790 B2 | 3/2010 | Indeck et al. |
| 7,689,366 B2 | 3/2010 | Duck et al. |
| 7,689,638 B2 | 3/2010 | Theimer et al. |
| 7,700,284 B2 | 4/2010 | Romanov |
| 7,702,595 B2 | 4/2010 | Shibuya et al. |
| 7,702,610 B2 | 4/2010 | Zane et al. |
| 7,711,491 B2 | 5/2010 | Vandersall et al. |
| 7,734,427 B2 | 6/2010 | Clark |
| 7,747,641 B2 | 6/2010 | Kim et al. |
| 7,756,847 B2 | 7/2010 | Paus et al. |
| 7,761,462 B2 | 7/2010 | Bjornson et al. |
| 7,769,708 B2 | 8/2010 | Caruso |
| 7,788,043 B2 | 8/2010 | Gill et al. |
| 7,788,279 B2 | 8/2010 | Mohajer et al. |
| 7,792,894 B1 | 9/2010 | Cohn et al. |
| 7,801,591 B1 | 9/2010 | Shusterman |
| 7,805,254 B2 | 9/2010 | Clark |
| 7,805,460 B2 | 9/2010 | Artan et al. |
| 7,807,375 B2 | 10/2010 | Cantor et al. |
| 7,809,509 B2 | 10/2010 | Milosavljevic |
| 7,809,510 B2 | 10/2010 | Milosavljevic |
| 7,822,782 B2 | 10/2010 | Chakravarty et al. |
| 7,831,392 B2 | 11/2010 | Antoniotti et al. |
| 7,853,410 B2 | 12/2010 | Selifonov et al. |
| 7,855,080 B2 | 12/2010 | Elliott |
| 7,856,322 B2 | 12/2010 | Kim et al. |
| 7,856,409 B2 | 12/2010 | Shibuya |
| 7,962,291 B2 | 6/2011 | Williams |
| 2002/0177138 A1 | 11/2002 | Boissy |
| 2006/0129331 A1 | 6/2006 | Akilesh et al. |
| 2007/0087368 A1 | 4/2007 | Loraine |
| 2007/0088510 A1 | 4/2007 | Li |
| 2007/0117140 A1 | 5/2007 | Iizumi |
| 2007/0118296 A1 | 5/2007 | SantaLucia |
| 2007/0122837 A1 | 5/2007 | Belshaw |
| 2007/0128631 A1 | 6/2007 | Hussan et al. |
| 2007/0134676 A1 | 6/2007 | Barrett |
| 2007/0134692 A1 | 6/2007 | Valmeekam |
| 2007/0141557 A1 | 6/2007 | Raab |
| 2007/0141612 A1 | 6/2007 | Kumar |
| 2008/0003571 A1 | 1/2008 | McKernan et al. |
| 2009/0035764 A1 | 2/2009 | Sampas |
| 2009/0062129 A1 | 3/2009 | McKernan et al. |
| 2011/0124111 A1 | 5/2011 | Hoshizaki et al. |
| 2011/0128545 A1 | 6/2011 | Cox et al. |

\* cited by examiner

SYSTEMS AND METHODS FOR SEQUENCE DATA ALIGNMENT QUALITY ASSESSMENT

RELATED APPLICATIONS

This application claims priority pursuant to 35 U.S.C. §119 (e) to U.S. Provisional Patent Application Ser. No. 61/361,879, entitled "Systems and Methods for Sequencing Data Alignment Quality Assessment," filed on Jul. 6, 2010, the entirety of which is incorporated herein by reference as if set forth in full.

FIELD

The present disclosure generally relates to the field of nucleic acid sequencing including systems and methods for mapping or aligning fragment sequence reads to a reference sequence.

INTRODUCTION

Upon completion of the Human Genome Project, one focus of the sequencing industry has shifted to finding higher throughput and/or lower cost nucleic acid sequencing technologies, sometimes referred to as "next generation" sequencing (NGS) technologies. In making sequencing higher throughput and/or less expensive, the goal is to make the technology more accessible for sequencing. These goals can be reached through the use of sequencing platforms and methods that provide sample preparation for larger quantities of samples of significant complexity, sequencing larger numbers of complex samples, and/or a high volume of information generation and analysis in a short period of time. Various methods, such as, for example, sequencing by synthesis, sequencing by hybridization, and sequencing by ligation are evolving to meet these challenges.

Research into fast and efficient nucleic acid (e.g., genome, exome, etc.) sequence assembly methods is vital to the sequencing industry as NGS technologies can provide ultra-high throughput nucleic acid sequencing. As such sequencing systems incorporating NGS technologies can produce a large number of short sequence reads in a relatively short amount time. Sequence assembly methods must be able to assemble and/or map a large number of reads quickly and efficiently (i.e., minimize use of computational resources). For example, the sequencing of a human size genome can result in tens or hundreds of millions of reads that need to be assembled before they can be further analyzed to determine their biological, diagnostic and/or therapeutic relevance.

Sequence assembly can generally be divided into two broad categories: de novo assembly and reference genome mapping assembly. In de novo assembly, sequence reads are assembled together so that they form a new and previously unknown sequence. Whereas in reference genome mapping, sequence reads are assembled against an existing backbone sequence (e.g., reference sequence, etc.) to build a sequence that is similar but not necessarily identical to the backbone sequence.

Conventional mapping tools (e.g., MAQ, BFAST, SHRiMP, BWA, etc.) used to align sequence reads tend to incorrectly estimate alignment quality compared to phred-scaled quality scores; as these tools typically do not support quality value determination that differentiates between read fragments types (e.g., single, mate-pair, paired-end, etc.).

SUMMARY

Systems, methods, software and computer-usable media for determining alignment quality of biomolecule-related sequence reads aligned to a reference sequence are disclosed. Biomolecule-related sequences can relate to proteins, peptides, nucleic acids, and the like, and can include structural and functional information such as secondary or tertiary structures, amino acid or nucleotide sequences, sequence motifs, binding properties, genetic mutations and variants, and the like.

In various embodiments, nucleic acid sequence read data can be generated using various techniques, platforms or technologies, including, but not limited to: capillary electrophoresis, microarrays, ligation-based systems, polymerase-based systems, hybridization-based systems, direct or indirect nucleotide identification systems, pyrosequencing, ion- or pH-based detection systems, electronic signature-based systems, etc.

In one aspect, a computer-implemented method for classifying alignments of paired nucleic acid sequence reads is disclosed. A plurality of paired nucleic acid sequence reads is received, wherein each read is comprised of a first tag and a second tag separated by an insert region. Potential alignments for the first and second tags of each paired nucleic acid sequence read to a reference sequence is determined, wherein the potential alignments satisfies a minimum threshold mismatch constraint. Potential paired alignments of the first and second tags of each read are identified, wherein a distance between the first and second tags of each potential paired alignment is within an estimated insert size range. An alignment score is calculated for each potential paired alignment based on a distance between the first and second tags and a total number of mismatches for each tag.

In another aspect, a system for identifying potential alignments for sequencing reads is disclosed. The system includes a nucleic acid sequencer and a processor in communications with the sequencer. The nucleic acid sequencer can be configured to interrogate a sample and produce a plurality of read sequences from the sample. The processor can be configured to obtain the read sequences from the sequencer, perform alignments of the read sequences from the sequencer to a reference sample, calculate a quality value for each alignment and output each alignment with its associated quality value.

In still another aspect, a computer-implemented method for determining possible alignments for sequencing reads is disclosed. A sample can be interrogated to produce a plurality of read sequences from the sample. Alignments are performed for the read sequences from the sequencer. A quality value for each alignment is determined. Each alignment with its associated quality value is outputted.

These and other features are provided herein.

DRAWINGS

For a more complete understanding of the principles disclosed herein, and the advantages thereof, reference is now made to the following descriptions taken in conjunction with the accompanying drawings, in which.

It is to be understood that the figures are not necessarily drawn to scale, nor are the objects in the figures necessarily drawn to scale in relationship to one another. The figures are depictions that are intended to bring clarity and understanding to various embodiments of apparatuses, systems, and methods disclosed herein. Wherever possible, the same reference numbers will be used throughout the drawings to refer to the same or like parts. Moreover, it should be appreciated that the drawings are not intended to limit the scope of the present teachings in any way.

DESCRIPTION OF VARIOUS EMBODIMENTS

Embodiments of systems and methods for determining sequence alignment quality are described herein.

The section headings used herein are for organizational purposes only and are not to be construed as limiting the described subject matter in any way.

In this detailed description of the various embodiments, for purposes of explanation, numerous specific details are set forth to provide a thorough understanding of the embodiments disclosed. One skilled in the art will appreciate, however, that these various embodiments may be practiced with or without these specific details. In other instances, structures and devices are shown in block diagram form. Furthermore, one skilled in the art can readily appreciate that the specific sequences in which methods are presented and performed are illustrative and it is contemplated that the sequences can be varied and still remain within the spirit and scope of the various embodiments disclosed herein.

All literature and similar materials cited in this application, including but not limited to, patents, patent applications, articles, books, treatises, and internet web pages are expressly incorporated by reference in their entirety for any purpose. Unless defined otherwise, all technical and scientific terms used herein have the same meaning as is commonly understood by one of ordinary skill in the art to which the various embodiments described herein belongs. When definitions of terms in incorporated references appear to differ from the definitions provided in the present teachings, the definition provided in the present teachings shall control.

It will be appreciated that there is an implied "about" prior to the temperatures, concentrations, times, etc. discussed in the present teachings, such that slight and insubstantial deviations are within the scope of the present teachings. In this application, the use of the singular includes the plural unless specifically stated otherwise. Also, the use of "comprise", "comprises", "comprising", "contain", "contains", "containing", "include", "includes", and "including" are not intended to be limiting. It is to be understood that both the foregoing general description and the following detailed description are exemplary and explanatory only and are not restrictive of the present teachings.

Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art. Standard techniques are used, for example, for nucleic acid purification and preparation, chemical analysis, recombinant nucleic acid, and oligonucleotide synthesis. Enzymatic reactions and purification techniques are performed according to manufacturer's specifications or as commonly accomplished in the art or as described herein. The techniques and procedures described herein are generally performed according to conventional methods well known in the art and as described in various general and more specific references that are cited and discussed throughout the instant specification. See, e.g., Sambrook et al., *Molecular Cloning: A Laboratory Manual* (Third ed., Cold Spring Harbor Laboratory Press, Cold Spring Harbor, N.Y. 2000). The nomenclatures utilized in connection with, and the laboratory procedures and techniques described herein are those well known and commonly used in the art.

As used herein, "a" or "an" means "at least one" or "one or more."

A "system" denotes a set of components, real or abstract, comprising a whole where each component interacts with or is related to at least one other component within the whole.

A "biomolecule" is any molecule that is produced by a biological organism, including large polymeric molecules such as proteins, polysaccharides, lipids, and nucleic acids as well as small molecules such as primary metabolites, secondary metabolites, and other natural products.

The phrase "next generation sequencing" or NGS refers to sequencing technologies having increased throughput as compared to traditional Sanger- and capillary electrophoresis-based approaches, for example with the ability to generate hundreds of thousands of relatively small sequence reads at a time. Some examples of next generation sequencing techniques include, but are not limited to, sequencing by synthesis, sequencing by ligation, and sequencing by hybridization. More specifically, the SOLiD Sequencing System of Life Technologies Corp. provides massively parallel sequencing with enhanced accuracy. The SOLiD System and associated workflows, protocols, chemistries, etc. are described in more detail in PCT Publication No. WO 2006/084132, entitled "Reagents, Methods, and Libraries for Bead-Based Sequencing," international filing date Feb. 1, 2006, U.S. patent application Ser. No. 12/873,190, entitled "Low-Volume Sequencing System and Method of Use," filed on Aug. 31, 2010, and U.S. patent application Ser. No. 12/873,132, entitled "Fast-Indexing Filter Wheel and Method of Use," filed on Aug. 31, 2010, the entirety of each of these applications being incorporated herein by reference thereto.

The phrase "sequencing run" refers to any step or portion of a sequencing experiment performed to determine some information relating to at least one biomolecule (e.g., nucleic acid molecule).

It is well known that DNA (deoxyribonucleic acid) is a chain of nucleotides consisting of 4 types of nucleotides; A (adenine), T (thymine), C (cytosine), and G (guanine), and that RNA (ribonucleic acid) is comprised of 4 types of nucleotides; A, U (uracil), G, and C. It is also known that certain pairs of nucleotides specifically bind to one another in a complementary fashion (called complementary base pairing). That is, adenine (A) pairs with thymine (T) (in the case of RNA, however, adenine (A) pairs with uracil (U)), and cytosine (C) pairs with guanine (G). When a first nucleic acid strand binds to a second nucleic acid strand made up of nucleotides that are complementary to those in the first strand, the two strands bind to form a double strand. As used herein, "nucleic acid sequencing data," "nucleic acid sequencing information," "nucleic acid sequence," "genomic sequence," "genetic sequence," or "fragment sequence," or "nucleic acid sequencing read" denotes any information or data that is indicative of the order of the nucleotide bases (e.g., adenine, guanine, cytosine, and thymine/uracil) in a molecule (e.g., whole genome, whole transcriptome, exome, oligonucleotide, polynucleotide, fragment, etc.) of DNA or RNA. It should be understood that the present teachings contemplate sequence information obtained using all available varieties of techniques, platforms or technologies, including, but not limited to: capillary electrophoresis, microarrays, ligation-based systems, polymerase-based systems, hybridization-based systems, direct or indirect nucleotide identification systems, pyrosequencing, ion- or pH-based detection systems, electronic signature-based systems, etc.

The phrase "ligation cycle" refers to a step in a sequence-by-ligation process where a probe sequence is ligated to a primer or another probe sequence.

The phrase "color call" refers to an observed dye color resulting from the detection of a probe sequence after a ligation cycle of a sequencing run.

The phrase "color space" refers to a nucleic acid sequence data schema where nucleic acid sequence information is represented by a set of colors (e.g., color calls, color signals, etc.) each carrying details about the identity and/or positional sequence of bases that comprise the nucleic acid sequence. For example, the nucleic acid sequence "ATCGA" can be represented in color space by various combinations of colors that are measured as the nucleic acid sequence is interrogated using optical detection-based (e.g., dye-based, etc.) sequencing techniques such as those employed by the SOLiD System. That is, in various embodiments, the SOLiD System can employ a schema that represents a nucleic acid fragment sequence as an initial base followed by a sequence of overlapping dimers (adjacent pairs of bases). The system can encode each dimer with one of four colors using a coding scheme that results in a sequence of color calls that represent a nucleotide sequence.

The phrase "base space" refers to a nucleic acid sequence data schema where nucleic acid sequence information is represented by the actual nucleotide base composition of the nucleic acid sequence. For example, the nucleic acid sequence "ATCGA" is represented in base space by the actual nucleotide base identities (e.g., A, T/or U, C, G) of the nucleic acid sequence.

A "polynucleotide", "nucleic acid", or "oligonucleotide" refers to a linear polymer of nucleosides (including deoxyribonucleosides, ribonucleosides, or analogs thereof) joined by internucleosidic linkages. Typically, a polynucleotide comprises at least three nucleosides. Usually oligonucleotides range in size from a few monomeric units, e.g. 3-4, to several hundreds of monomeric units. Whenever a polynucleotide such as an oligonucleotide is represented by a sequence of letters, such as "ATGCCTG," it will be understood that the nucleotides are in 5'→3' order from left to right and that "A" denotes deoxyadenosine, "C" denotes deoxycytidine, "G" denotes deoxyguanosine, and "T" denotes thymidine, unless otherwise noted. The letters A, C, G, and T may be used to refer to the bases themselves, to nucleosides, or to nucleotides comprising the bases, as is standard in the art.

The techniques of "paired-end," "pairwise," "paired tag," or "mate pair" sequencing are generally known in the art of molecular biology (Siegel A. F. et al., Genomics. 2000, 68: 237-246; Roach J. C. et al., Genomics. 1995, 26: 345-353). These sequencing techniques can allow the determination of multiple "reads" of sequence, each from a different place on a single polynucleotide. Typically, the distance (i.e., insert region) between the two reads or other information regarding a relationship between the reads is known. In some situations, these sequencing techniques provide more information than does sequencing two stretches of nucleic acid sequences in a random fashion. With the use of appropriate software tools for the assembly of sequence information (e.g., Mullikin J. C. et al., Genome Res. 2003, 13: 81-90; Kent, W. J. et al., Genome Res. 2001, 11: 1541-8) it is possible to make use of the knowledge that the "paired-end," "pairwise," "paired tag" or "mate pair" sequences are not completely random, but are known to occur a known distance apart and/or to have some other relationship, and are therefore linked or paired in the genome. This information can aid in the assembly of whole nucleic acid sequences into a consensus sequence.

Computer-Implemented System

Figure 1:
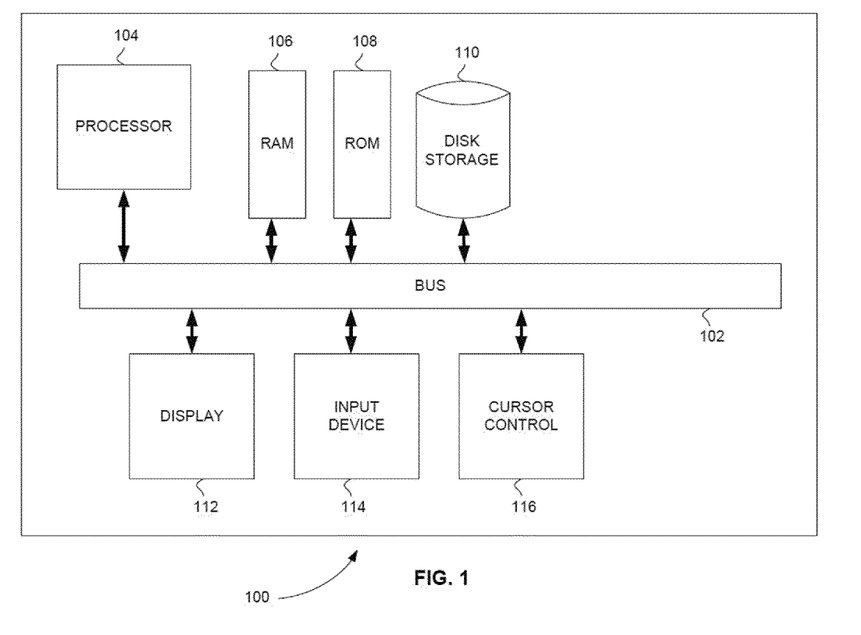
FIG. 1 is a block diagram that illustrates a computer system, in accordance with various embodiments.

FIG. 1 is a block diagram that illustrates a computer system 100, upon which embodiments of the present teachings may be implemented. In various embodiments, computer system 100 can include a bus 102 or other communication mechanism for communicating information, and a processor 104 coupled with bus 102 for processing information. In various embodiments, computer system 100 can also include a memory 106, which can be a random access memory (RAM) or other dynamic storage device, coupled to bus 102 for determining base calls, and instructions to be executed by processor 104. Memory 106 also can be used for storing temporary variables or other intermediate information during execution of instructions to be executed by processor 104. In various embodiments, computer system 100 can further include a read only memory (ROM) 108 or other static storage device coupled to bus 102 for storing static information and instructions for processor 104. A storage device 110, such as a magnetic disk or optical disk, can be provided and coupled to bus 102 for storing information and instructions.

In various embodiments, computer system 100 can be coupled via bus 102 to a display 112, such as a cathode ray tube (CRT) or liquid crystal display (LCD), for displaying information to a computer user. An input device 114, including alphanumeric and other keys, can be coupled to bus 102 for communicating information and command selections to processor 104. Another type of user input device is a cursor control 116, such as a mouse, a trackball or cursor direction keys for communicating direction information and command selections to processor 104 and for controlling cursor movement on display 112. This input device typically has two degrees of freedom in two axes, a first axis (i.e., x) and a second axis (i.e., y), that allows the device to specify positions in a plane.

A computer system 100 can perform the present teachings. Consistent with certain implementations of the present teachings, results can be provided by computer system 100 in response to processor 104 executing one or more sequences of one or more instructions contained in memory 106. Such instructions can be read into memory 106 from another computer-readable medium, such as storage device 110. Execution of the sequences of instructions contained in memory 106 can cause processor 104 to perform the processes described herein. Alternatively hard-wired circuitry can be used in place of or in combination with software instructions to implement the present teachings. Thus implementations of the present teachings are not limited to any specific combination of hardware circuitry and software.

The term "computer-readable medium" as used herein refers to any media that participates in providing instructions to processor 104 for execution. Such a medium can take many forms, including but not limited to, non-volatile media, volatile media, and transmission media. Examples of non-volatile media can include, but are not limited to, optical or magnetic disks, such as storage device 110. Examples of volatile media can include, but are not limited to, dynamic memory, such as memory 106. Examples of transmission media can include, but are not limited to, coaxial cables, copper wire, and fiber optics, including the wires that comprise bus 102.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, PROM, and EPROM, a FLASH-EPROM, any other memory chip or cartridge, or any other tangible medium from which a computer can read.

Various forms of computer readable media can be involved in carrying one or more sequences of one or more instructions to processor 104 for execution. For example, the instructions can initially be carried on the magnetic disk of a remote computer. The remote computer can load the instructions into its dynamic memory and send the instructions over a telephone line using a modem. A modem local to computer system 100 can receive the data on the telephone line and use an infra-red transmitter to convert the data to an infra-red signal. An infra-red detector coupled to bus 102 can receive the data carried in the infra-red signal and place the data on bus 102. Bus 102 can carry the data to memory 106, from which processor 104 retrieves and executes the instructions. The instructions received by memory 106 may optionally be stored on storage device 110 either before or after execution by processor 104.

In accordance with various embodiments, instructions configured to be executed by a processor to perform a method are stored on a computer-readable medium. The computer-readable medium can be a device that stores digital information. For example, a computer-readable medium includes a compact disc read-only memory (CD-ROM) as is known in the art for storing software. The computer-readable medium is accessed by a processor suitable for executing instructions configured to be executed.

Nucleic Acid Sequencing Platforms

Nucleic acid sequence data can be generated using various techniques, platforms or technologies, including, but not limited to: capillary electrophoresis, microarrays, ligation-based systems, polymerase-based systems, hybridization-based systems, direct or indirect nucleotide identification systems, pyrosequencing, ion- or pH-based detection systems, electronic signature-based systems, etc.

Figure 2:
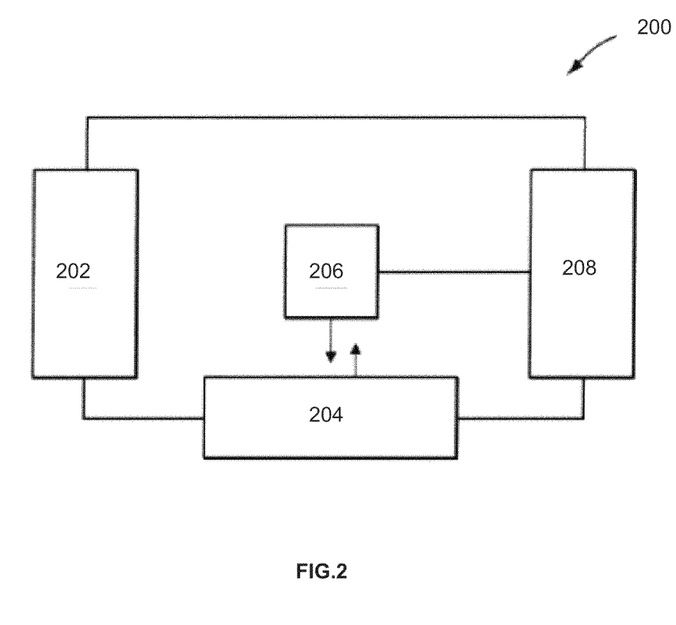
FIG. 2 is a schematic diagram of a system for reconstructing a nucleic acid sequence, in accordance with various embodiments.

Various embodiments of nucleic acid sequencing platforms (i.e., nucleic acid sequencer) can include components as displayed in the block diagram of FIG. 2. According to various embodiments, sequencing instrument 200 can include a fluidic delivery and control unit 202, a sample processing unit 204, a signal detection unit 206, and a data acquisition, analysis and control unit 208. Various embodiments of instrumentation, reagents, libraries and methods used for next generation sequencing are described in U.S. Patent Application Publication No. US20090062129 (application Ser. No. 11/737,308) and U.S. Patent Application Publication No. US20080003571 (application Ser. No. 11/345,979) to McKernan, et al., which applications are incorporated herein by reference. Various embodiments of instrument 200 can provide for automated sequencing that can be used to gather sequence information from a plurality of sequences in parallel, i.e., substantially simultaneously.

In various embodiments, the fluidics delivery and control unit 202 can include reagent delivery system. The reagent delivery system can include a reagent reservoir for the storage of various reagents. The reagents can include RNA-based primers, forward/reverse DNA primers, oligonucleotide mixtures for ligation sequencing, nucleotide mixtures for sequencing-by-synthesis, optional ECC oligonucleotide mixtures, buffers, wash reagents, blocking reagent, stripping reagents, and the like. Additionally, the reagent delivery system can include a pipetting system or a continuous flow system which connects the sample processing unit with the reagent reservoir.

In various embodiments, the sample processing unit 204 can include a sample chamber, such as flow cell, a substrate, a micro-array, a multi-well tray, or the like. The sample processing unit 204 can include multiple lanes, multiple channels, multiple wells, or other means of processing multiple sample sets substantially simultaneously. Additionally, the sample processing unit can include multiple sample chambers to enable processing of multiple runs simultaneously. In particular embodiments, the system can perform signal detection on one sample chamber while substantially simultaneously processing another sample chamber. Additionally, the sample processing unit can include an automation system for moving or manipulating the sample chamber.

In various embodiments, the signal detection unit 206 can include an imaging or detection sensor. For example, the imaging or detection sensor can include a CCD, a CMOS, an ion sensor, such as an ion sensitive layer overlying a CMOS, a current detector, or the like. The signal detection unit 206 can include an excitation system to cause a probe, such as a fluorescent dye, to emit a signal. The excitation system can include an illumination source, such as arc lamp, a laser, a light emitting diode (LED), or the like. In particular embodiments, the signal detection unit 206 can include optics for the transmission of light from an illumination source to the sample or from the sample to the imaging or detection sensor. Alternatively, the signal detection unit 206 may not include an illumination source, such as for example, when a signal is produced spontaneously as a result of a sequencing reaction. For example, a signal can be produced by the interaction of a released moiety, such as a released ion interacting with an ion sensitive layer, or a pyrophosphate reacting with an enzyme or other catalyst to produce a chemiluminescent signal. In another example, changes in an electrical current can be detected as a nucleic acid passes through a nanopore without the need for an illumination source.

In various embodiments, data acquisition analysis and control unit 208 can monitor various system parameters. The system parameters can include temperature of various portions of instrument 200, such as sample processing unit or reagent reservoirs, volumes of various reagents, the status of various system subcomponents, such as a manipulator, a stepper motor, a pump, or the like, or any combination thereof.

It will be appreciated by one skilled in the art that various embodiments of instrument 200 can be used to practice variety of sequencing methods including ligation-based methods, sequencing by synthesis, single molecule methods, nanopore sequencing, and other sequencing techniques. Ligation sequencing can include single ligation techniques, or change ligation techniques where multiple ligation are performed in sequence on a single primary. Sequencing by synthesis can include the incorporation of dye labeled nucleotides, chain termination, ion/proton sequencing, pyrophosphate sequencing, or the like. Single molecule techniques can include continuous sequencing, where the identity of the nuclear type is determined during incorporation without the need to pause or delay the sequencing reaction, or staggered sequence, where the sequencing reactions is paused to determine the identity of the incorporated nucleotide.

In various embodiments, the sequencing instrument 200 can determine the sequence of a nucleic acid, such as a polynucleotide or an oligonucleotide. The nucleic acid can include DNA or RNA, and can be single stranded, such as ssDNA and RNA, or double stranded, such as dsDNA or a RNA/cDNA pair. In various embodiments, the nucleic acid can include or be derived from a fragment library, a mate pair library, a ChIP fragment, or the like. In particular embodiments, the sequencing instrument 200 can obtain the sequence information from a single nucleic acid molecule or from a group of substantially identical nucleic acid molecules.

In various embodiments, sequencing instrument 200 can output nucleic acid sequencing read data in a variety of different output data file types/formats, including, but not limited to: *.fasta, *.csfasta, *seq.txt, *qseq.txt, *.fastq, *.sff, *prb.txt, *.sms, *srs and/or *.qv.

Classifying Alignments of Paired Reads

Figure 3:
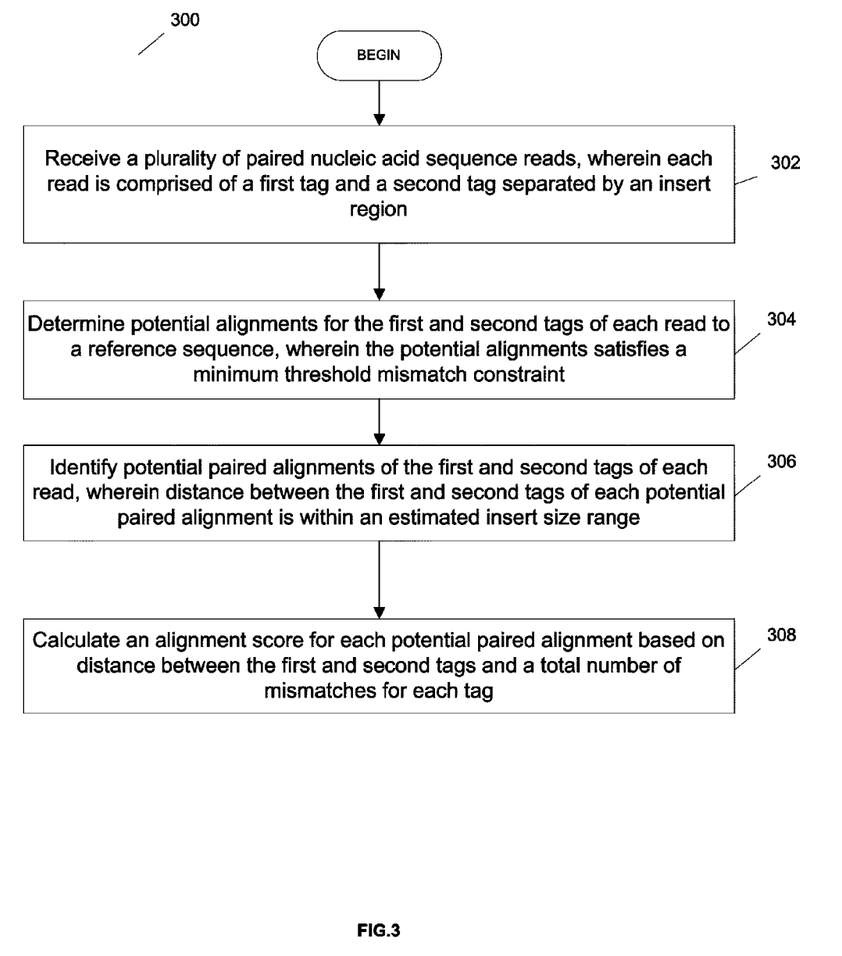
FIG. 3 is an exemplary flowchart showing a method for classifying alignment quality of paired reads, in accordance with various embodiments.

FIG. 3 is an exemplary flowchart showing a method for classifying alignments of paired nucleic acid sequence reads, in accordance with various embodiments. In various embodiments, the sequence read alignment classification scores can be a factor in the pairing quality value (PQV) determining.

As depicted herein, method 300 begins with step 302 where a plurality of paired nucleic acid sequence reads is received. Each paired nucleic acid sequence read is comprised of a first tag (e.g., F3/R3 read) and a second tag (e.g., F3/R3 read) separated by an insert region. In various embodiments, the paired nucleic acid sequence reads are mate-pair reads. In various embodiments, the paired nucleic acid sequence reads are paired-end reads. In various embodiments, the paired nucleic acid sequence reads are a combination of mate-pair and paired-end reads.

In step 304, the potential alignments for the first and second tags of each of each paired nucleic acid sequence read to a reference sequence are determined, wherein all the potential alignments satisfy a minimum threshold mismatch constraint. That is, each read tag that is aligned to the reference sequence cannot exceed a certain number of mismatches (i.e., minimum threshold mismatch constraint).

In step 306, potential paired alignments of the first and second tags of each paired nucleic acid sequence read are identified, wherein a distance between the first and second tags of each potential paired alignment is within an estimated insert size range. In various embodiments, the estimated insert size range can be determined by: 1. mapping all the tags to a reference sequence, 2. determining a distribution of pairing distance for all uniquely mapped pairs of tags, and 3. calculating a mean and standard deviation value from the distribution pairing distance data to estimate a range of insert size (e.g., range values that covers 95% of the distributed distances of the observed pairs, range values derived a certain number of standard deviation from the mean, etc.).

In step 308, an alignment score is calculated for each potential paired alignment based on the distance between the first and second tags and a total number of mismatches for each tag. In various embodiments, the alignment score calculation is also a function of read alignment length (i.e., read length of the tags). In various embodiments, the alignment score calculation is also a function of the total number of possible alignment for each paired nucleic acid sequence read.

In various embodiments, the method 300 can be performed using color space nucleic acid sequence data. In various embodiments, the method 300 can be performed using base space nucleic acid sequence data. It should be understood, however, that the method 300 disclosed herein can be performed using any schema or format of nucleic acid sequence information as long as the schema or format can convey the base identity and position.

Pairing/Mapping Quality Values

According to various embodiments, the system and methods of the present teachings may introduce a Bayesian inference based statistical approach to calculating mapping quality values for different library types such as single fragment and paired reads (e.g., mate-pair, paired-end reads, etc.). These approaches can make use of mate-pair/paired-end read information including insert size distribution between the read pairs (e.g., pairs of tags), read orientation, strand ID annotations, gene ID annotations, etc. Using this approach, non-uniform prior probabilities for different alignment types and alignments that correspond to inversions (e.g., mate-pair reads mapping to opposite strands, etc.), gapped alignments (e.g., insertion/deletion within a read) can be assigned and can be useful to assess the probability of observing such mutations in a particular genome.

In various embodiments, for the case of whole-transcriptome sequencing, mate-pair/paired-end reads capable of being mapped to exons from the same gene can be assigned a uniform prior probability regardless of the genomic distance between the exons. In various embodiments, mate-pair/paired-end reads that map to exons from different genes (corresponding to gene fusions) can be assigned a lower prior probability. In various embodiments such an approach cam be implemented in sequence analytics tools and applications such as for example SOLiD LIFESCOPE genetic analysis software (Life Technologies Corporation; Carlsbad, Calif.) and can be used for mapping and variant detection using sequencing reads such as those obtained from a NGS sequencing instrument.

In various embodiments, the accuracy and predictive value of the mapping/pairing quality score computed using these methods can be demonstrated using either simulated datasets (for example from a human reference chromosome 0) as well as actual genome datasets (for example from a HuRef sample generated using a NGS instrument). Evaluating the resulting mapping quality values and compared to phred-scale values for probability of misalignment demonstrates that the methods of the present teachings provide more accurate mapping quality when compared against conventional approaches and may be better suited to represent phred-scale alignment probability for a multiplicity of different library types.

According to various embodiments, the mapping quality methods described herein demonstrate highly accurate and comprehensive functionality in terms of computing quality of different alignment types including gapped alignments and whole-transcriptomes. In one aspect, the predictive value of a mapping quality value can improve the efficiency of generating variant calls and gene fusion calls made using various tools and sequencing analytics software (such as the SOLiD LIFESCOPE sequence analysis toolset). Together with the base quality values of individual bases in a read, mapping quality values can be used to improve the efficiency of rare-allele detection in cancer genomics research.

In various embodiments, methods for determining Mapping/Pairing quality value (PQV) are provided. The PQV can be generally associated with a phred-scaled quantitative measure of the confidence of aligning a read to the correct location in the reference genome. The PQV may further be represented as the negative log odds of misaligning a read ($-10 \log_{10}[\text{prob of error}]$).

In various embodiments, the posterior probability of correctly aligning a read pair to a reference sequence can be calculated using (for example) the total alignment length of the mate pair reads, total number of mismatches to reference, complete mate-pair information such as insert size and gene ID annotations (in the case of whole transcriptome). The calculated mapping/pairing quality values can further represent the probability of aligning sequenced reads to the reference sequence (e.g., reference genome, etc.).

According to various embodiments, a method is provided which can be implemented in a software tool or application which computes mapping/paring quality values that better represents phred-scale quality scores (for example the probability of misaligning the reads). This method can make use of read pair information to compute quality values for mate-pair and paired-end library types. Mapping/pairing quality values computed by the methods of the present teachings can be accurate and predictive in terms of being able to improve the accuracy of small variant detection.

Exemplary Methods for Calculating Pairing Quality Values

In various embodiments, the pairing algorithm of the present teachings can be configured to report multiple sets of possible alignments for any given pair of reads (for example F3/R3 tags for a Mate-pair run and F3/F5-P2 tags for a Paired-end run obtained using a NGS sequencer). The pairing quality method and algorithm can implement a Bayesian approach to calculate the quality of a given alignment for a pair of reads (i.e., pair of tags) and the alignment with the highest PQV can be selected as the primary alignment for the pair of reads. In various embodiments, the PQVs may be used to represent a Phred-Scaled quality score. Such an approach can be useful for downstream variant detection tools such as DiBayes, Small-InDels, Large-InDels and CNV.

In various aspects, the quality of any given alignment for a pair of reads $r_1$, $r_2$ mapped to positions $x_1$ and $x_2$ in the reference sequence can be represented by Equation 1:

$$Q(r_1,r_2,x_1,x_2)=P(A(r_1,r_2,x_1,x_2)|r_1,r_2),$$

where $A(r_1,r_2,x_1,x_2)$ represents the event when reads $r_1$ & $r_2$ are sequenced from locations $x_1$ & $x_2$ respectively and $P(A|r_1,r_2)$ is the probability of the event A occurring given the pair of reads r1 and r2.

Applying a Bayesian-type approach, the posterior probability $P(A|r_1,r_2)$ may be represented as Equation 2:

$$P(A(r_1, r_2, x_1, x_2)|r_1, r_2) = \frac{P(r_1, r_2 | A) \times P(A)}{P(r_1, r_2)}$$

The probability $P(r_1,r_2)$, of observing reads $r_1$ and $r_2$ can then be a function of the complexity of the genome sequenced. One exemplary probability determination can be calculated as Equation 3:

$$P(r_1,r_2)=\Sigma_{i,j\in M}P(r_1,r_2|A(r_1,r_2,i,j))\times P(A(r_1,r_2,i,j))$$

where M is the set of possible alignments to the reference sequence for reads $r_1$ and $r_2$. Using this relationship to represent $P(r_1, r_2)$ in the previous equation one obtains Equation 4:

$$P(A(r_1, r_2, x_1, x_2)|r_1, r_2) = \frac{P(r_1, r_2 | A(r_1, r_2, x_1, x_2)) \times P(A(r_1, r_2, x_1, x_2))}{\sum_{i,j} P(r_1, r_2 | A(r_1, r_2, i, j)) \times P(A(r_1, r_2, i, j))}$$

The prior probability P(A) of the event A can further be given by Equation 5:

$$P(A(r_1,r_2,x_1,x_2))=P(A(r_2,x_2)|B)\times P(B(r_1,x_1)),$$

where $B(r_1,x_1)$ is the event that read $r_1$ is sequenced from location $x_1$ in the genome and P(A|B) is the conditional probability of finding the event A where read $r_2$ is sequenced from location $x_2$, given that read $r_1$ was sequenced from location $x_1$.

The probability P(B) can be a constant for any given read $r_1$, and the conditional probability P(A|B) can follow the insert-size distribution. As indicated below, the following prior probabilities can be used in pairing quality calculations. In various embodiments, $P(A(r,r_2,i,j))$ can be the alignment score calculated for each potential sequence pair alignment (as discussed above with respect to FIG. 3).

P(A|B)=1, for all 'AAA' pairs.

P(A|B)=1/10,000, for all 'non-AAA' pairs (including Small & Large Indels).

P(A|B)=1/10,000, when one of the reads in the pair cannot be mapped to the reference sequence.

In various embodiments, where a pair of reads have a unique set of alignments to a reference sequence, the posterior probability $P(A|r_1, r_2)$ can result in 1 thereby obscuring the relative quality of the alignment compared to those of other read pairs. This can be addressed by calculating a background probability P(B), which can represent the probability of finding an alignment to the reference sequence with M+1 mismatches, where M is the maximum allowed mismatches set in the pairing.ini file, as shown in Equation 6:

$$P_B=P(r_1|A(r_1,x_1)\times P(r_2|B,M+1 \text{ mismatches}),r_1>r_2 \\ (k_1>k_2, \text{if } r_1=r_2)$$

For uniquely paired reads, the posterior probability can be given by Equation 7:

$$P(A(r_1, r_2, x_1, x_2)|r_1, r_2) = \frac{P(r_1, r_2 | A)}{P(r_1, r_2 | A) + P_B}$$

For mapping using a local alignment method, the likelihood function $P(r_1,r_2|A)$ can be given by Equation 8:

$$P(r_1, r_2 | A) = (1-e)^{(k_1+k_2)-(m_1+m_2)} \times e^{(m_1+m_2)} \times \left(\frac{1}{4}\right)^{(L_1+L_2)-(m_1+m_2)}$$

where,
$L_1$ & $L_2$ are the read lengths for reads $r_1$ and $r_2$ respectively, (ex. F3=50 and R3=50),
$k_1$ & $k_2$ are the alignment lengths ($k_1 \leq L_1$ and $k_2 \leq L_2$),
$m_1$ & $m_2$ are the number of mismatches, and
e is the error rate.

Being consistent with a phred-type quality score ($-10*\log_{10}[\text{prob(error)}]$), the PQV may be computed as the negative log odds of misaligning the pair of reads, as shown in Equation 9:

$$PQV=-10\times\log_{10}[1-Q(r_1,r_2,x_1,x_2)]$$

The resulting pairing quality values can be normalized by a maximum value to help ensure that the pairing quality values are within a desired range [0,100], as shown in Equation 10:

$$PQV = \frac{PQV}{PWV_{max}} \times 100$$

$PQV_{max}$ can reflect an exemplary maximum possible pairing quality value when the pair of reads map uniquely to the reference with zero mismatches.

Exemplary Methods for Calculating PQVs for Gapped Alignments

In various embodiments, a pairing method can be devised to search for gapped alignments (i.e., InDels) when one of the tag (F3/R3/F5-P2) maps to a reference sequence and another tag does not map to the reference sequence within a selected insert-size range. For this exemplary approach, where both an un-gapped and a gapped alignment are found for a given read then, due to the low prior probability of 10^-4 assigned to the gapped alignments, the PQV for gapped alignments can be approximately zero.

Figure 4:
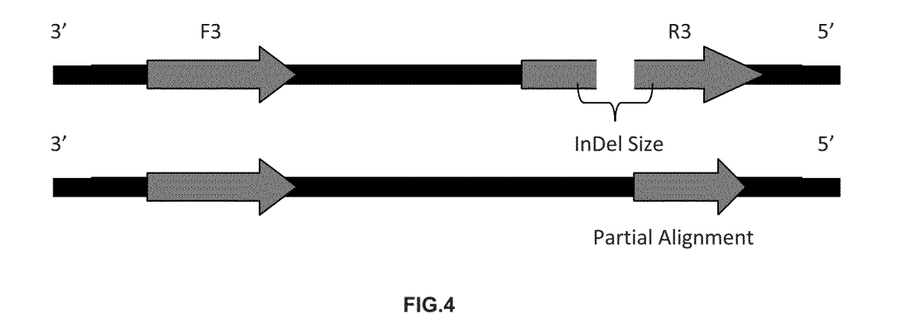
FIG. 4 is a depiction of how PQV can be calculated for gapped alignments, in accordance with various embodiments.

Thus, as shown in FIG. 4, in calculating the PQV for gapped alignments, an alternative hypothesis can be tested as the probability of finding the partial un-gapped alignments. The read with the gapped alignment can be treated as two partial reads on either side of an InDel start point where the half with the greatest length is used as the partial alignment length for an alternate hypothesis. Such an approach can be used to help ensure that gapped alignments within InDel starting point at the middle of the read with significant length of alignment on either side of the InDel starting point will be assigned a higher PQV compared to gapped alignments with InDel starting point close to either ends of the read, as shown in Equation 11:

$$P(A|r)_{InDel} = \frac{P(r|A)_{InDel}}{P(r|A)_{InDel} + P_{PartialAlignment}}$$

In various embodiments, for reads with multiple un-gapped alignments, the read with the highest PQV can be selected as the primary alignment for the read and is reported to the *.BAM file. In cases where there are multiple alignments with the same PQV, then the primary alignment can be selected at random from among the alignments with the same PQV.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

Further, in describing various embodiments, the specification may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process should not be limited to the performance of their steps in the order written, and one skilled in the art can readily appreciate that the sequences may be varied and still remain within the spirit and scope of the various embodiments.

The embodiments described herein, can be practiced with other computer system configurations including hand-held devices, microprocessor systems, microprocessor-based or programmable consumer electronics, minicomputers, mainframe computers and the like. The embodiments can also be practiced in distributing computing environments where tasks are performed by remote processing devices that are linked through a network.

It should also be understood that the embodiments described herein can employ various computer-implemented operations involving data stored in computer systems. These operations are those requiring physical manipulation of physical quantities. Usually, though not necessarily, these quantities take the form of electrical or magnetic signals capable of being stored, transferred, combined, compared, and otherwise manipulated. Further, the manipulations performed are often referred to in terms, such as producing, identifying, determining, or comparing.

Any of the operations that form part of the embodiments described herein are useful machine operations. The embodiments, described herein, also relate to a device or an apparatus for performing these operations. The systems and methods described herein can be specially constructed for the required purposes or it may be a general purpose computer selectively activated or configured by a computer program stored in the computer. In particular, various general purpose machines may be used with computer programs written in accordance with the teachings herein, or it may be more convenient to construct a more specialized apparatus to perform the required operations.

Certain embodiments can also be embodied as computer readable code on a computer readable medium. The computer readable medium is any data storage device that can store data, which can thereafter be read by a computer system. Examples of the computer readable medium include hard drives, network attached storage (NAS), read-only memory, random-access memory, CD-ROMs, CD-Rs, CD-RWs, magnetic tapes, and other optical and non-optical data storage devices. The computer readable medium can also be distributed over a network coupled computer systems so that the computer readable code is stored and executed in a distributed fashion.

What is claimed is:

1. A method for classifying alignments of paired nucleic acid sequence reads, comprising:
   disposing a nucleic acid sample within a sample chamber of a sequencing instrument, the nucleic acid sample comprising a plurality of target nucleic acids, the target nucleic acids including first and second tags, the first tag being derived from a first region of a polynucleotide and the second tag being derived from a second region of the polynucleotide, the first and second tags being separated by an insert region;
   detecting, by a detection device, a plurality of signals representative of the sequence of at least one of the target nucleic acids of the nucleic acid sample;
   generating, by a computing device comprising a processor and memory, a paired nucleic acid sequence read from the plurality of signals, the paired nucleic acid sequence read including a first read of the first tag and second read of the second tag;
   determining, by the computing device, potential alignments for the first and second reads of the paired nucleic acid sequence read to a reference sequence, wherein each potential alignment satisfies a minimum threshold mismatch constraint;
   identifying, by the computing device, potential paired alignments of the paired nucleic acid sequence read, wherein a distance between the first and second reads of each potential paired alignment is within an estimated insert size range; and
   calculating, by the computing device, an alignment score for each potential paired alignment based on:
   a distance between the first and second reads, and
   a total number of mismatches for the first and second reads.

2. The method for classifying alignments of paired nucleic acid sequence reads, as recited in claim 1, wherein the paired nucleic acid sequence read is a mate-pair read.

3. The method for classifying alignments of paired nucleic acid sequence reads, as recited in claim 1, wherein the paired nucleic acid sequence read is a paired-end read.

4. The method for classifying alignments of paired nucleic acid sequence reads, as recited in claim 1, wherein the estimated insert size range is a standard deviation of a distribution of insert sizes of the insert regions of the aligned paired nucleic acid sequence reads.

5. The method for classifying alignments of paired nucleic acid sequence reads, as recited in claim 1, wherein the calculated alignment score is a function of read alignment length.

6. The method for classifying alignments of paired nucleic acid sequence reads, as recited in claim 1, wherein the calculated alignment score is a function of a total number of possible alignments for each read.

7. A system for identifying potential alignments for sequencing reads, comprising:
   a sequencing instrument comprising:
      a sample processing unit configured to accept a nucleic acid sample, the nucleic acid sample comprising a plurality of target nucleic acids, the target nucleic acids including first and second tags, the first tag being derived from a first region of a polynucleotide and the second tag being derived from a second region of the polynucleotide, the first and second tags being separated by an insert region;
      a reagent delivery system configured to provide reagents for sequencing the target nucleic acids to the sample processing unit;
      a signal detection unit configured to detect a plurality of signals during sequencing, the signals representative of a sequence of at least one of the target nucleic acids; and
   a computer processor in communication with the sequencer, the processor configured to:
      generate a paired nucleic acid sequence read from the plurality of signals,
      the paired nucleic acid sequence read including a first read of the first tag and second read of the second tag,
      perform alignments of the paired nucleic acid sequence read to a reference sequence,
      calculate a quality value for the respective alignments, the quality value being a function of the distance between the first and second reads, and a total number of mismatches for the first and second reads, and
      output each alignment with its associated quality value.

8. The system for identifying potential alignments for sequencing reads, as recited in claim 7, wherein aligned paired nucleic acid sequence reads have insert region sizes that fall within an estimated insert size range for the aligned paired nucleic acid sequence reads.

9. The system for identifying potential alignments for sequencing reads, as recited in claim 8, wherein the estimated insert size range is based on a standard deviation value derived from a distribution insert sizes of the insert regions of the aligned paired nucleic acid sequence reads.

10. A method for determining possible alignments for sequencing reads, comprising:
    disposing a nucleic acid sample within a sample chamber of a sequencing instrument, the nucleic acid sample comprising a plurality of target nucleic acids, the target nucleic acids including first and second tags, the first tag being derived from a first region of a polynucleotide and the second tag being derived from a second region of the polynucleotide, the first and second tags being separated by an insert region;
    detecting, by a detection device, a plurality of signals representative of the sequence of at least one of the target nucleic acids of the nucleic acid sample;
    generating, by a computing device comprising a processor and memory, a paired nucleic acid sequence read from the plurality of signals, the paired nucleic acid sequence read including a first read of the first tag and second read of the second tag;
    performing, by the computing device, alignments of the paired nucleic acid sequence read;
    calculating, by the computing device, a quality value for the alignments, the quality value being a function of the distance between the first and second reads, and a total number of mismatches for the first and second reads; and
    outputting, by the computing device, respective alignments and associated quality values.

11. The computer-implemented method for determining possible alignments for sequencing reads, as recited in claim 10, wherein the calculated quality value for each alignment is a function of read alignment length.

12. The computer-implemented method for determining possible alignments for sequencing reads, as recited in claim 10, wherein aligned paired nucleic acid sequence reads have insert region sizes that fall within an estimated insert size range for the aligned paired reads.

13. The computer-implemented method for determining possible alignments for sequencing reads, as recited in claim 12, wherein the estimated insert size range is based on a standard deviation value derived from a distribution of insert sizes of the insert regions of the aligned paired nucleic acid sequence reads.

* * * * *